US012715829B2

(12) United States Patent
Shemesh et al.

(10) Patent No.: US 12,715,829 B2
(45) Date of Patent: Aug. 25, 2026

(54) MIXTURE OF 3-HEXEN-1-OL ISOMERS AND A PROCESS OF PREPARING SAME

(71) Applicant: Agan Aroma & fine chemicals Ltd., Ashdod (IL)

(72) Inventors: Sasson Shemesh, Rehovot (IL); Remo Barak Almog, Yavne (IL); Shani Shoushan, Rishon le-Zion (IL); Rotem Sella-Erez, Tel Aviv (IL)

(73) Assignee: AGAN AROMA & FINE CHEMICALS LTD., Ashdod (IL)

( * ) Notice: Subject to any disclaimer, the term of this patent is extended or adjusted under 35 U.S.C. 154(b) by 968 days.

(21) Appl. No.: 17/798,076

(22) PCT Filed: Feb. 4, 2021

(86) PCT No.: PCT/IL2021/050138

§ 371 (c)(1),
(2) Date: Aug. 7, 2022

(87) PCT Pub. No.: WO2021/156870

PCT Pub. Date: Aug. 12, 2021

(65) Prior Publication Data

US 2023/0150905 A1 May 18, 2023

Related U.S. Application Data

(60) Provisional application No. 62/970,766, filed on Feb. 6, 2020.

(51) Int. Cl.
*C07C 33/025* (2006.01)
*A61K 8/34* (2006.01)

(52) U.S. Cl.
CPC .............. *C07C 33/025* (2013.01); *A61K 8/34* (2013.01)

(58) Field of Classification Search
USPC .......................................................... 560/261
See application file for complete search history.

(56) References Cited

U.S. PATENT DOCUMENTS

| | | | |
|---|---|---|---|
| 9,834,626 | B2 | 12/2017 | Chisholm et al. |
| 10,577,560 | B2 | 3/2020 | Avidor et al. |
| 2010/0087351 | A1 | 4/2010 | Fadel et al. |
| 2011/0104089 | A1 | 5/2011 | Wohrle et al. |
| 2020/0002255 | A1 | 1/2020 | Parvulescu |

FOREIGN PATENT DOCUMENTS

| | | |
|---|---|---|
| CN | 101166702 | 4/2008 |
| CN | 101180287 | 5/2008 |
| CN | 101875599 | 11/2010 |
| CN | 110325497 | 10/2019 |
| EP | 3290087 | 3/2018 |
| JP | 2010-523543 | 7/2010 |
| WO | WO 2006/116419 | 11/2006 |
| WO | WO 2008/120175 | 10/2008 |
| WO | WO 2015/186699 | 12/2015 |
| WO | WO 2021/156870 | 8/2021 |
| WO | WO 2021/156870 A8 | 8/2021 |
| WO | WO 2023/199324 | 10/2023 |

OTHER PUBLICATIONS

Machine translation of CN101875599A.*

International Search Report and the Written Opinion Dated May 11, 2021 From the International Searching Authority Re. Application No. PCT/IL2021/050138. (10 Pages).

Lopez-Gresa et al. "A Non-targeted Metabolomics Approach Unravels the VOCs Associated with the Tomato Immune Response against Pseudomonas Syringae", Frontiers in Plant Science, 8: 1-15, Jul. 4, 2017.

Scala et al. "Green Leaf Volatiles: A Plant's Multifunctional Weapon against Herbivores and Pathogens", Molecular Research in Plant Secondary Metabolism, International Journal of Molecular Sciences, 14(9): 17781-17811, Aug. 30, 2013.

Supplementary European Search Report and the European Search Opinion Dated Feb. 19, 2024 From the European Patent Office Re. Application No. 21750779.7. (8 Pages).

Snider et al. "Diaklylaluminum Chloride Catalyzed Ene Reactions of Aldehydes. Synthesis of Ipsenol", Tetrahedron Letters, 21(19): 1815-1818, Jan. 29, 1980.

International Preliminary Report on Patentability Dated Oct. 24, 2024 From the International Bureau of WIPO Re. Application No. PCT/IL2023/050391. (9 Pages).

International Search Report and the Written Opinion Dated Jul. 14, 2023 From the International Searching Authority Re. Application No. PCT/IL2023/050391 (18 Pages).

Al-Kateb et al. "The Relationship Between Growth Stages and Aroma Composition of Lemon Basil Ocimum Citriodorum Vis", Food Chemistry, 152: 440-446, Jun. 1, 2014. Abstract.

Janzantti et al. "HS—GC—MS—O Analysis and Sensory Acceptance of Passion Fruit During Maturation", Journal of Food Science and Technology, 54(8): 2594-2601, May 8, 2017. Abstract.

(Continued)

*Primary Examiner* — Ana Z Muresan

(74) *Attorney, Agent, or Firm* — ROTHWELL, FIGG, ERNST & MANBECK, P.C.

(57) ABSTRACT

Compositions comprising 3-hexen-1-ol are described herein, as well as odor-imparting formulations comprising same and articles-of-manufacturing comprising such compositions or odor-imparting formulations. The compositions comprise trans-3-hexen-1-ol in a range of from 67% to 82% by weight and cis-3-hexen-1-ol in a range of from 18% to 33% by weight, wherein a total concentration of trans-3-hexen-1-ol and cis-3-hexen-1-ol is at least 97% by weight. Further described herein is a process for preparing a composition comprising 3-hexen-1-ol, the process comprising: contacting 1-pentene with a formaldehyde in the presence of a Lewis acid to thereby obtain a crude mixture comprising 3-hexen-1-ol; and contacting the mixture comprising 3-hexen-1-ol with a base.

10 Claims, 4 Drawing Sheets

(56) References Cited

OTHER PUBLICATIONS

Polidoro et al. "Characterization of Volatile Fractions in Green Mate and Mate Leaves (Ilex Paraguariensis A. St. Hil.) by Comprehensive Two-Dimensional Gas Chromatography Coupled to Time-of-Flight Mass Spectrometry (GC × GC/TOFMS)", Microchemical Journal, 128: 118-127, Sep. 2016. Abstract.
Soares et al. "Volatile and Non-Volatile Chemical Composition of the White Guava Fruit (Psidium Guajava) at Different Stages of Maturity", Food Chemistry, 100(1): 15-21, 2007. Abstract.
Examination Report Under Sections 12 & 13 of the Patents Act, 1970 and the Patents Rules, 2003 Dated Sep. 4, 2025 From the Government of India, Intellectual Property India, Patents, Designs, Trade Marks, Geographical Indications, The Patent Office Re. Application No. 202227047978. (5 Pages).
Jin et al. "Synthesis of 4-Chloro-6-Phenyl-2-(2-Oxopropyl)Tetrahydropyran", Journal of Yanbian Univer sity (Natural Science), 35(3): 242-245, Sep. 2009. (Abstract).
Wen et al. "Highly Selective Synthesis of Tetrahydropyranes by Prins-cyclization Mediated by Tin ( • ) Chloride", Chemical Journal of Chinese Universities, 26(3): 452-455, 2005. (Abstract).
Notice of Reasons for Rejection Dated Oct. 29, 2024 From the Japan Patent Office Re. Application No. 2022-547928 and its Translation Into English. (9 Pages).
Hans et al. "Cis-3-Hexenyl Hexanoate ED", Food and Chemical Toxicology, 30: 45, XP023810950, Jan. 1, 1992.
Hans et al. "Cis-3-Hexenyl Valerate ED", Food and Chemical Toxicology, 30: 47, XP023810951, Jan. 1, 1992.
Opdyke et al. "Cis-3-Hexanyl Benzoate", Food and Cosmetics Toxicology, 16(5-6): 773, XP023859192, Dec. 1, 1978.
Opdyke et al. "Monographs on Fragrance Raw Materials", Food and Cosmetics Toxicology, 17(4): 357-363, 365, XP023866659, Jan. 1, 1979.
Notification of Office Action and Search Report Dated Mar. 20, 2024 From the State Intellectual Property Office of the People's Republic of China Re. Application No. 202180017926.X. (8 Pages).
Translation Dated Mar. 26, 2024 of Notification of Office Action and Search Report Dated Mar. 20, 2024 From the State Intellectual Property Office of the People's Republic of China Re. Application No. 202180017926.X. (4 Pages).
Metzger et al. "Aluminiumchloride-Induced Additions of Ormaldehyde to Alkenes", Bulletin des Sociétés Chimiques Belges, 103(7-8): 393-397, Dec. 31, 1994.
Office Action Dated Feb. 19, 2025 From the Israel Patent Office Re. Application No. 295343. (3 Pages).

* cited by examiner

MIXTURE OF 3-HEXEN-1-OL ISOMERS AND A PROCESS OF PREPARING SAME

RELATED APPLICATIONS

This application is a National Phase of PCT Patent Application No. PCT/IL2021/050138 having International filing date of Feb. 4, 2021, which claims the benefit of priority under 35 USC § 119 (e) of U.S. Provisional Patent Application No. 62/970,766 filed on Feb. 6, 2020. The contents of the above applications are all incorporated herein by reference as if fully set forth herein in their entirety.

FIELD AND BACKGROUND OF THE INVENTION

The present invention, in some embodiments thereof, relates to odoriferous substances and, more particularly, but not exclusively, to a novel odoriferous mixture of cis-3-hexen-1-ol and trans-3-hexen-1-ol, to formulations and products containing same to a process of preparing same.

Odoriferous substances are widely used in fields such as beverages, cosmetics, sanitary and hygienic goods, detergents, bath refreshing additives, medicines, and agricultural chemicals. Odoriferous substances are used for imparting scent, odor, aroma or fragrance to the product.

A fragrance (or scent, odor, or aroma) results from a combination of a variety of components in a fragrance composition. Ordinarily, fragrances are created by blending odoriferous substances, optionally along with carrier and other chemical materials. These materials are blended in order to achieve what are known as "top note", "middle note" and "bottom note" components.

A "top note" is the quality perceived immediately upon application. A "base note" is the essence of the fragrance. It typically consists of large, heavy molecules that evaporate slowly. Some base notes are perceived more than 24 hours after application. The "middle note" is the perceived quality that bridges from top to base note. It typically emerges after the top note.

In recent years, green note fragrances have been of particular interest. The fresh aroma of freshly cut green grass fragrance-imparting agents are used in, for example, perfumery, candles, potpourri, bath and body products, melt-and-pour soap, cold process soap, gel wax, and the like, and also for imparting a grass scent to artificial grass or turf.

The most recognized green note-imparting odoriferous substance is cis-3-hexen-1-ol, which is also referred to in the art (Z)-3-hexen-1-ol, cis-3-hexenol, (z)-3-hexenol, and is also known as "leaf alcohol". Other green note-imparting agents which are widely used in the industry include, for example, n-hexanal, n-hexanol, (E)-2-hexenal (trans-2-hexenal), (E)-2-hexen-1-ol (trans hexen-1-ol), and (Z)-3-hexenal (cis-3-hexenal), and ester derivatives thereof.

Extracting leaf alcohol and other grass-scent imparting substances from green plants and leaves typically involve high production costs and low production amounts and are therefore commercially ineffective. In addition, the demand for green notes has grown to exceed their supply from traditional natural sources such as mint (*Mentha arvensis*) oil and other plant oils. This has motivated research efforts toward finding alternative ways of obtaining these materials.

U.S. Patent Application Publication No. 2018/0037913 teaches methods of producing hexenols by using enzymatic processes.

Synthetic processes for preparing cis-3-hexen-1-ol and derivatives thereof have been developed in the past decades. These typically involve selective dehydrogenation of 3-hexyn-1-ol or of a conjugated enolate, and may use various starting materials. Reference is made, for example, to R K Singh, E Singh, Handbook of Meat, Poultry and Seafood, 2007; J. Dorsky, Perfumes: Art, Science and Technology, 2012; "fragrance chemistry and technology," Zhao Yi Bin, Chemical Industry Press, 2007.

CN Patent Application Publication No. CN 1244518 teaches a synthetic method that utilizes 1,3-pentadiene, and 2-methyl-5,6-dihydrofuran through ring-opening.

CN Patent Application Publication No. CN 101875599 teaches a reaction between 1-pentene and formaldehyde, formalin, paraformaldehyde or trioxane, in the presence of a Lewis acid catalyst, which is followed by work-up procedures, and distillation under reduced pressure, to thereby provide a mixture of geraniol and cis-3-hexen-1-ol. This mixture is then purified to give the cis-3-hexen-1-ol. In one example, when paraformaldehyde and aluminum chloride where used, a mixture of geraniol and trans-3-hexen-1-ol was obtained.

Additional background art includes WO 2006/116419, which describes separation of E and Z isomers of an alkene alcohol, such as hexenol, or derivative thereof, by continuously contacting an ion exchange medium with silver and/or copper ions with a feed stream comprising the E and Z isomers of the alkene alcohol or derivative thereof.

SUMMARY OF THE INVENTION

According to an aspect of some embodiments of the invention, there is provided a process for preparing a composition comprising 3-hexen-1-ol, the process comprising:

- contacting 1-pentene with a formaldehyde in the presence of a Lewis acid to thereby obtain a crude (first) mixture comprising 3-hexen-1-ol (also referred to herein as a crude first mixture); and
- contacting the (crude first) mixture comprising 3-hexen-1-ol with a base,
- thereby obtaining the composition comprising 3-hexen-1-ol.

According to an aspect of some embodiments of the invention, there is provided a composition comprising trans-3-hexen-1-ol at a concentration in a range of from 67% to 82% by weight and cis-3-hexen-1-ol at a concentration in a range of from 18% to 33% by weight, wherein a total concentration of the trans-3-hexen-1-ol and the cis-3-hexen-1-ol is at least 97% by weight (e.g., as determined by gas chromatography as described herein in the Examples section that follows).

According to an aspect of some embodiments of the invention, there is provided an odor-imparting formulation comprising a composition comprising 3-hexen-1-ol to the composition being as described herein in any of the respective embodiments and any combination thereof.

According to an aspect of some embodiments of the invention, there is provided an odor-imparting formulation comprising a composition comprising 3-hexen-1-ol, the composition being obtainable by a process according to any of the respective embodiments described herein and any combination thereof.

According to an aspect of some embodiments of the invention, there is provided an article-of-manufacturing comprising an odor-imparting formulation according to any of the respective embodiments described herein.

According to some of any of the embodiments of the invention relating to a process, the process comprises:

(a) contacting 1-pentene with a formaldehyde in the presence of a Lewis acid to thereby obtain a crude (first) mixture comprising 3-hexen-1-ol;

(b) distilling the crude (first) mixture to thereby obtain a (first) mixture enriched in 3-hexen-1-ol (also referred to herein as a first mixture); and (c) contacting the (first) mixture enriched in 3-hexen-1-ol with the base.

According to some of any of the embodiments of the invention relating to a process, the process further comprises separating the 3-hexen-1-ol from the mixture following the contacting with the base, to thereby obtain the composition comprising 3-hexen-1-ol.

According to some of any of the embodiments of the invention relating to separating the 3-hexen-1-ol, the separating of the 3-hexen-1-ol comprises distillation (e.g., as described in the Examples section that follows).

According to some of any of the embodiments of the invention relating to a process, a ratio of trans-3-hexen-1-ol to cis-3-hexen-1-ol in the crude (first) mixture is in a range of from 7:3 to 8:2 (trans:cis).

According to some of any of the embodiments of the invention relating to a process, contacting the (first) mixture with the base reduces an amount of at least one chlorinated tetrahydropyran by elimination of chlorine atoms (e.g., elimination of HCl).

According to some of any of the embodiments of the invention relating to reducing an amount of at least one chlorinated tetrahydropyran, the at least one chlorinated tetrahydropyran comprises 3-ethyl-4-chloro-tetrahydropyran.

According to some of any of the embodiments of the invention relating to reducing an amount of the at least one chlorinated tetrahydropyran, a concentration of 3-ethyl-4-chloro-tetrahydropyran following the contacting with the base is no more than 0.1%, or no more than 0.05% by weight.

According to some of any of the embodiments of the invention relating to reducing an amount of the at least one chlorinated tetrahydropyran, a total concentration of chlorinated tetrahydropyrans following the contacting with the base is no more than 0.1% by weight.

According to some of any of the embodiments of the invention relating to a process, contacting 1-pentene with the formaldehyde is effected by contacting the 1-pentene with 1,3,5-trioxane (e.g., as a precursor of formaldehyde).

According to some of any of the embodiments of the invention relating to a process, contacting 1-pentene with the formaldehyde comprises adding a mixture containing the 1-pentene and formaldehyde to the Lewis acid, over the course of (during a time period of) no more than two hours. It should be noted that depending on the reaction volume and addition rate, other time period are contemplated, for example, of up to 24 hours, or 20 hours, or 18 hours, or 16 hours, or 12 hours, or 10 hours, or 8 hours, etc.

According to some of any of the embodiments of the invention relating to a process, the Lewis acid is or comprises $AlCl_3$.

According to some of any of the embodiments of the invention, a concentration of 3-hexen-1-ol in the composition is at least 97% by weight.

According to some of any of the embodiments of the invention, the composition comprises trans-3-hexen-1-ol at a concentration in a range of from 67% to 82% by weight and cis-3-hexen-1-ol at a concentration in a range of from 18% to 33% by weight.

According to some of any of the embodiments of the invention, a total concentration of 2-hexen-1-ol and 4-hexen-1-ol in the composition is no more than 0.25% by weight.

According to some of any of the embodiments of the invention, a concentration of 3-ethyl-4-chloro-tetrahydropyran in the composition is no more than 0.05% by weight.

According to some of any of the embodiments of the invention, a total concentration of chlorinated tetrahydropyrans in the composition is no more than 0.1% by weight.

According to some of any of the embodiments of the invention, a ratio of trans-3-hexen-1-ol to cis-3-hexen-1-ol in the composition is in a range of from 7:3 to 8:2 (trans:cis).

According to some of any of the embodiments of the invention, the composition further comprises 1-hexanol, at a concentration of no more than 5%, or no more than 4%, or no more than 3%, or no more than 2%, by weight.

According to some of any of the embodiments of the invention, the composition further comprises 1-hexanol, at a concentration of from 0.01 to 5%, or from 0.01 to 4%, or from 0.01 to 3%, or from 0.01 to 2%, or from 0.1 to 5%, or from 0.1 to 4%, or from 0.1 to 3%, or from 0.1 to 2%, or from 1 to 5%, or from 1 to 4%, or from 1 to 3%, or from 1 to 2%, by weight, including any intermediate values and subranges therebetween.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
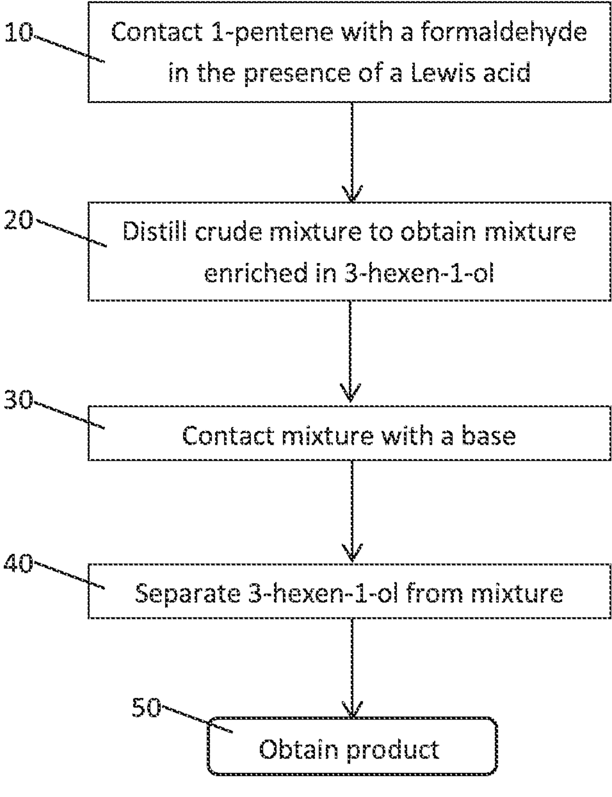
FIG. 1 presents a flow chart depicting an exemplary process of preparing a product (a composition) comprising 3-hexen-1-ol, according to some embodiments of the invention.

The present invention, in some embodiments thereof, relates to odoriferous substances and, more particularly, but not exclusively, to a novel odoriferous mixture of cis-3-hexen-1-ol and trans-3-hexen-1-ol, to formulations and products containing same to a process of preparing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed in the Background section hereinabove, cis-3-hexen-1-ol and trans-3-hexen-1-ol are green note-imparting agents which are widely used in the industry. Synthetic processes for preparing these compounds, which are cost effective and provide compositions featuring high purity are therefore desirable. Importantly, such processes which provide such odor-imparting composition and are devoid of byproducts that may mask or alter the odor of the odor-imparting agents are desirable.

The inventors have uncovered that preparation of 3-hexen-1-ol by reacting 1-pentene with a formaldehyde can result, via a relatively simple and inexpensive process, in a combination of cis-3-hexen-1-ol and trans-3-hexen-1-ol in a ratio characterized by particularly desirable odor.

The inventors have further uncovered that preparation of 3-hexen-1-ol by reacting 1-pentene with a formaldehyde commonly results in substantial levels of chlorinated pyran derivatives as byproducts, which may negatively affect the odor of the composition and/or cause the product to be considered unsuitable for applications (e.g., involving ingestion) in which non-toxicity is of high importance, and cannot be separated from the 3-hexen-1-ol without difficulty. This phenomenon presents a problem of choosing between reduced quality of the product and costly separation techniques.

Following laborious experimentation, the inventors have further uncovered that the abovementioned problem can be solved by effecting elimination of chlorine atoms (e.g., elimination of HCl) of the chlorinated pyran derivatives, to obtain elimination products which can readily and efficiently be separated from the 3-hexen-1-ol by simple techniques such as distillation. While reducing the present invention to practice, the inventors have prepared compositions of 3-hexen-1-ol (using $AlCl_3$ as Lewis acid) in large scales and at high purity, without requiring undue effort.

Embodiments of the present invention thus relate to a composition comprising cis-3-hexen-1-ol and/or trans-3-hexen-1-ol with low levels of byproducts, a process for preparing such a composition, and odor-imparting formulations and articles-of-manufacturing containing such a composition (or formulation). Embodiments of the present invention further relate to a novel composition which comprises a mixture of trans-3-hexen-1-ol and cis-3-hexen-1-ol at a ratio of from 6:4 to 9:1 (trans:cis), and more particularly, from 67:33 to 82:18 (trans:cis).

Composition:

According to an aspect of some embodiments of the invention, there is provided a composition comprising trans-3-hexen-1-ol in a range of from 67% to 82% by weight of the composition, and cis-3-hexen-1-ol in a range of from 18% to 33% by weight of the composition.

As exemplified herein, compositions having the above-mentioned concentrations of trans-3-hexen-1-ol and cis-3-hexen-1-ol exhibit particularly desirable odor, and can be readily prepared without impurities or byproducts at a level which negatively affects the product. That is, the compositions are such that a level of impurities or byproducts that may affect the product (e.g., odor properties of the product) is sufficiently low or null such that their effect is substantially nullified.

According to an aspect of some embodiments of the invention, there is provided a composition comprising 3-hexen-1-ol (e.g., at a concentration of at least 50% by weight of the composition, or at least 60% or at least 70% or at least 80% or at least 90% by weight of the composition, according to any of the respective embodiments described herein) with a low concentration of byproducts, such as chlorinated pyrans (e.g., chlorinated tetrahydropyrans). In some such embodiments, a concentration of trans-3-hexen-1-ol in the composition is in a range of from 67% to 82% by weight. In some such embodiments, a concentration of cis-3-hexen-1-ol in the composition is in a range of from 18% to 33% by weight. In some such embodiments, the concentration of trans-3-hexen-1-ol is in a range of from 67% to 82% by weight, and the concentration of cis-3-hexen-1-ol is in a range of from 18% to 33% by weight.

Herein, the terms "3-hexen-1-ol" and "3-hexenol" (which are used interchangeably herein) refer to trans-3-hexen-1-ol and/or cis-3-hexen-1-ol, including combinations thereof, unless specifically indicated otherwise.

The 3-hexenol in the composition (according to any of the respective embodiments described herein) optionally comprises a combination of trans-3-hexen-1-ol and cis-3-hexen-1-ol, wherein a ratio of trans-3-hexen-1-ol to cis-3-hexen-1-ol in the composition is in a range of from about 6:4 to about 9:1 (trans:cis). In some embodiments, the ratio of trans-3-hexen-1-ol to cis hexen-1-ol in the composition is in a range of from about 7:3 to about 8:2 (trans:cis).

Herein, the terms "chlorinated pyran" and "chlorinated pyran derivative" (which are used interchangeably herein) refer to any pyran, dihydropyran and/or tetrahydropyran, which is substituted by one or more chlorine atom(s), and is optionally substituted by one or more additional substituents (e.g., alkyl).

Herein, the terms "chlorinated tetrahydropyran" and "chlorinated tetrahydropyran derivative" (which are used interchangeably herein) refer to tetrahydropyran, which is substituted by one or more chlorine atom(s), and is optionally substituted by one or more additional substituents (e.g., alkyl).

Examples of substituents of a pyran derivative include, without limitation, hydroxy (—OH), alkyl (e.g., $C_{1-4}$-alkyl, such as methyl or ethyl), alkenyl (e.g., $C_{2-4}$-alkenyl, such as vinyl) and alkoxy, wherein the alkyl, alkenyl and/or alkoxy may be unsubstituted or substituted (e.g., by hydroxy and/or chloro). Ethyl is an exemplary substituent.

In some of any of the embodiments described herein, according to any of the aspects described herein, a total concentration of chlorinated pyrans in the composition is no more than 0.5% by weight, optionally no more than 0.2% by weight, optionally no more than 0.1% by weight, optionally no more than 0.05% by weight, optionally no more than 0.02% by weight, optionally no more than 0.01% by weight, and optionally no more than 0.005% by weight.

In some of any of the embodiments described herein, according to any of the aspects described herein, a total concentration of chlorinated tetrahydropyrans in the composition is no more than 0.5% by weight, optionally no more than 0.2% by weight, optionally no more than 0.1% by weight, optionally no more than 0.05% by weight, optionally no more than 0.02% by weight, optionally no more than 0.01% by weight, and optionally no more than 0.005% by weight.

Figure 2:
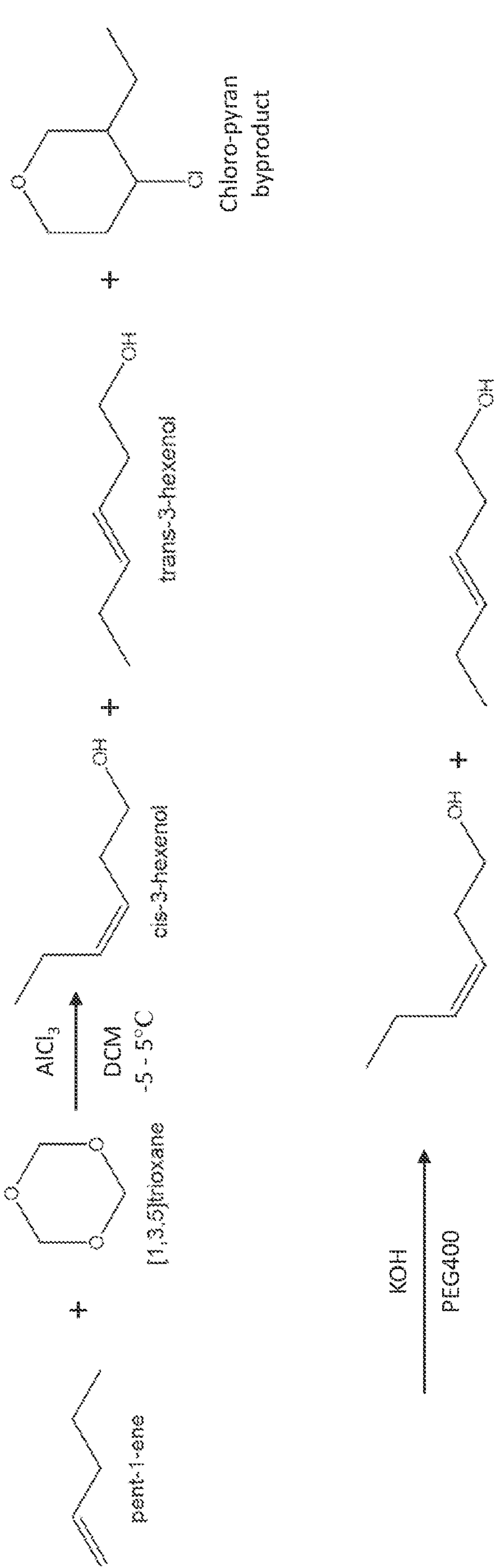
FIG. 2 presents a synthetic scheme for an exemplary preparation of 3-hexen-1-ol from 1-pentene and trioxane according to some embodiments of the invention, including elimination of chlorine (as HCl) from a chlorinated pyran derivative (chloro-pyran) byproduct.

3-Ethyl-4-chloro-tetrahydropyran is an exemplary chlorinated tetrahydropyran, according to some embodiments of the invention (see, FIG. 2).

Without being bound by any particular theory, it is believed that preparation of 3-hexenol, at least according to some embodiments, is particularly susceptible to contamination by 3-ethyl-4-chloro-tetrahydropyran, such that compositions with a low concentration of 3-ethyl-4-chloro-tetrahydropyran (according to any of the respective embodiments described herein) are advantageous.

In some of any of the embodiments described herein, the composition has a low concentration of 3-ethyl-4-chloro-tetrahydropyran, for example, no more than 0.2% by weight, optionally no more than 0.1% by weight, optionally no more than 0.05% by weight, optionally no more than 0.02% by weight, optionally no more than 0.01% by weight, and optionally no more than 0.005% by weight.

Additional examples of byproducts for which reduced concentrations are advantageous are isomers of 3-hexenol, such as 4-hexen-1-ol and 2-hexen-1-ol.

In some of any of the embodiments described herein, according to any of the aspects described herein, a total concentration of 4-hexen-1-ol and 2-hexen-1-ol in the composition is no more than 1% by weight, and optionally no more than 0.5% by weight.

In some of any of the embodiments described herein, the composition is substantially devoid of 4-hexen-1-ol and 2-hexen-1-ol.

Herein, the term "substantially devoid" refers to a concentration (for example, a total concentration of 4-hexen-1-ol and 2-hexen-1-ol) which is no more than 0.25% by weight, optionally no more than 0.1% by weight, optionally no more than 0.05% by weight, optionally no more than 0.025% by weight, optionally no more than 0.01% by weight, optionally no more than 0.005% by weight, optionally no more than 0.0025% by weight, and optionally no more than 0.001% by weight.

In some of any of the respective embodiments described herein, the concentration of 3-hexenol (i.e., total concentration of trans-3-hexen-1-ol and cis-3-hexen-1-ol) is at least 95%, or at least 96%, or at least 97% by weight of the composition. In some such embodiments, the concentration of 3-hexenol is at least 98% by weight of the composition. In some embodiments, the concentration of 3-hexenol is at least 99% by weight of the composition. In some embodiments, the concentration of 3-hexenol is at least 99.5% by weight of the composition. In some embodiments, the concentration of 3-hexenol is at least 99.8% by weight of the composition. In some embodiments, the concentration of 3-hexenol is at least 99.9% by weight of the composition.

In some of any of the respective embodiments described herein, the composition when analyzed by gas chromatography is devoid of a peak at a retention time of about 10.9 minutes or 11.3 minutes, when analysis is preferably performed under the following conditions (and exemplified in the Examples section): injection volume of 1 μl, and column (e.g., ZB-WAX column) with polyethylene glycol capillary column phase, 30 m length, 0.25 mm internal diameter, 0.25 μm film thickness, 16.371 psi head pressure; a temperature program of increasing from 50° C. to 100° C. at a rate of 5° C. per minute, then from 100° C. to 220° C. at a rate of 10° C. per minute, followed by 3 minutes at 220° C. (total of 25 minutes); and optionally using a flame ionization detector with a temperature of 260° C., air flow of 360 ml/minute, $H_2$ flow of 30 ml/minute and He makeup of 24.8 ml/minute.

In some of any of the respective embodiments described herein, the composition when analyzed by gas chromatography as described herein is characterized by peak at about 9.5 minutes and/or a peak at about 9.95 minutes (e.g., associated with trans- and cis-3-hexen-1-ol, respectively), and is devoid of a peak at a retention time which is about 1.0 minute or about 1.35 minute longer than the peak of about 9.9 minutes, and/or devoid of a peak at a retention time which is about 1.45 minute or about 1.8 minute longer than the peak of about 9.5 minutes (when analysis is preferably performed under the abovementioned conditions).

Herein, "devoid of a peak" refers to absence of a peak having an area of at least 0.1% an area of the main product, as indicated by the largest peak in the gas chromatography spectrum (e.g., trans-3-hexen-1-ol or cis-3-hexen-1-01).

In some of any of the embodiments described herein, the composition further comprises 1-hexanol, at a concentration of at a concentration of from 0.01 to 5%, or from 0.01 to 4%, or from 0.01 to 3%, or from 0.01 to 2%, or from 0.1 to 5%, or from 0.1 to 4%, or from 0.1 to 3%, or from 0.1 to 2%, or from 1 to 5%, or from 1 to 4%, or from 1 to 3%, or from 1 to 2%, by weight, including any intermediate values and subranges therebetween.

In some of any of the embodiments described herein, a composition as described herein in any of the respective embodiments is obtainable by a process according to any of the embodiments described herein relating to a process.

Herein throughout, whenever % by weight is indicated, it is as determined by means or methods known in the art. In some embodiments, the % by weight are as determined by gas chromatography, for example, quantitative gas chromatography, under conditions as described herein).

Process:

According to an aspect of some embodiments of the invention, there is provided a process of preparing a composition comprising 3-hexen-1-ol.

According to some embodiments of the present invention, the composition is as described herein in any of the respective embodiments and any combination thereof.

According to embodiments of the present invention, the process comprises contacting 1-pentene with a formaldehyde in the presence of a Lewis acid to thereby obtain a crude mixture comprising 3-hexen-1-ol (which is also referred to herein as a first mixture), and contacting an obtained mixture (e.g., first mixture) comprising 3-hexen-1-ol with a base.

FIG. 1 depicts a process according to some embodiments of the invention. As shown therein, the process begins at 10, by contacting 1-pentene with a formaldehyde in the presence of a Lewis acid (e.g., according to any of the respective embodiments described herein), to provide a crude first mixture, and is optionally followed by 20, by distilling the crude first mixture (e.g., a mixture obtained in step 10) to obtain a first mixture which is enriched in 3-hexen-1-ol (e.g., according to any of the embodiments described herein to distillation of a crude first mixture). The process then proceeds to 30, by contacting the first mixture (e.g., a mixture obtained in step 20 and/or in step 10) with a base (e.g., according to any of the embodiments described herein relating to contacting with a base), to obtain a second mixture (e.g., a crude second mixture), and is optionally followed by 40, by separation of 3-hexen-1-ol from the mixture obtained upon contacting with a base (mixture obtained in step 30), for example, by distillation (e.g., according to any of the embodiments described herein relating to separating 3-hexen-1-ol). At step 50, a product (e.g., a composition comprising 3-hexen-1-ol according to any of the respective embodiments described herein) is obtained.

As exemplified herein, it was uncovered that one or more chlorinated pyran derivatives (e.g., a chlorinated tetrahydropyran, such as 3-ethyl-4-chloro-tetrahydropyran) are commonly obtained as impurities—for example, at a concentration of 4% by weight of the crude mixture or more, and/or a concentration which is about 10% or more of the concentration of 3-hexenol obtained—that such an impurity may be difficult to separate from 3-hexenol via distillation, and that contacting the mixture of 3-hexenol with a base (according to any of the respective embodiments described herein) can be effective at converting the impurity to one or more compound which is more readily separated from the 3-hexenol (e.g., by distillation), by elimination of chlorine atoms (so as to obtain a molecule without a chlorine atom, e.g., comprising a carbon-carbon double bond in place of each chlorine atom).

In some embodiments, contacting 1-pentene with a formaldehyde in the presence of a Lewis acid effects a reaction between 1-pentene and the formaldehyde to form 3-hexenol (FIG. 1, step 10; FIG. 2).

The Lewis acid preferably acts as a catalyst of a reaction described herein. The Lewis acid may optionally be present in catalytic amount (i.e., in an amount considerably lower than that of the 1-pentene and formaldehyde). For example, the molar ratio of Lewis acid to 1-pentene and/or formaldehyde may optionally be no more than 0.8, or no more than 0.7, or no more than 0.6, or no more than 0.5, or no more than 0.4, or no more than 0.3, or no more than 0.2, or no more than 0.1.

In some of any of the respective embodiments described herein, the molar ratio of Lewis acid to 1-pentene and/or formaldehyde is at least 0.01 (e.g., from 0.01 to 0.8), or at least 0.05 (e.g., from 0.05 to 0.8), or at least 0.1 (e.g., from 0.1 to 0.8), or at least 0.2 (e.g., from 0.2 to 0.8), or at least 0.4 (e.g., from 0.4 to 0.8).

By "Lewis acid" it is meant, as commonly accepted in the art, a compound or species with is an acceptor of a pair of electrons. Examples of Lewis acids include without limitation, compounds based on metals such as aluminum, boron, silicon, tin, titanium, zirconium, iron, copper, and zinc, which are typically substituted by one or more electron withdrawing groups, such as one or more halo atoms (e.g., fluoro, chloro, or bromo), e.g., $BF_3$, $AlCl_3$, $TiCl_4$, $ZnCl_2$, and $BCl_3$. Such Lewis acids can optionally be substituted, in addition to one or more halo atoms, by one or more hydrocarbon groups such as alkyl, cycloalkyl, or aryl and/or by one or more nitrile (cyano) substituents. The total number of substituents depends on the valency of the metal.

The Lewis acid may optionally be in a liquid form (e.g., in solution or in suspension) and/or a solid form, such as granules, flakes, powder, and the like.

In some of any of respective embodiments described herein, the Lewis acid comprises at least one chlorine atom, which may optionally be a source of chlorine for generation of a chlorinated pyran derivative.

$AlCl_3$ (a.k.a. aluminum chloride) is a non-limiting example of a (chlorine-containing) Lewis acid, which may be used according to any of the embodiments described herein relating to a Lewis acid. In some such embodiments, the $AlCl_3$ is in a granular form. $AlCl_3$ may optionally be present in catalytic amount (according to any of the respective embodiments described herein), for example, a molar ratio of $AlCl_3$ to 1-pentene and/or formaldehyde may optionally be no more than 0.8, no more than 0.7, or no more than 0.6, or no more than 0.5, or no more than 0.4, or no more than 0.3, or no more than 0.2, or no more than 0.1.

In some of any of the respective embodiments described herein, the molar ratio of $AlCl_3$ to 1-pentene and/or formaldehyde is at least 0.01 (e.g., from 0.01 to 0.8), or at least 0.05 (e.g., from 0.05 to 0.8), or at least 0.1 (e.g., from 0.1 to 0.8), or at least 0.2 (e.g., from 0.2 to 0.8), or at least 0.4 (e.g., from 0.4 to 0.8). In exemplary embodiments, the molar ratio of $AlCl_3$ to 1-pentene and/or formaldehyde is about 0.6.

Alternatively or additionally, the (chlorine-containing) Lewis acid may be another chloride of aluminum, for example, an alkyl aluminum dichloride (i.e., $RAlCl_2$, wherein R is alkyl) or a dialkyl aluminum chloride (i.e., R'R"AlCl, wherein R' and R" are each an alkyl). Examples of such Lewis acids include, without limitation, $CH_3AlCl_2$ and $(CH_3)_2AlCl$. Also contemplated are nitrile-substituted aluminum chloride, where R' and/or R" is nitrile (cyano).

Additional examples of (chlorine-containing) Lewis acids include, without limitation, boron chlorides (e.g., $BCl_3$), iron chlorides (e.g., $FeCl_3$), tin chlorides (e.g., $SnCl_4$) and titanium chlorides (e.g., $TiCl_4$), and alkylated derivatives thereof as described hereinabove.

The reaction may optionally be monitored by observing the color of the reaction mixture, which in some embodiments, is preferably yellow. A brown color may be indicative of polymerization and heavy compound formation, which may result in lower yields.

Herein, the phrase "a formaldehyde" encompasses formaldehyde per se (i.e., $H_2C{=}O$) as well as any compound known in the art to release formaldehyde and/or be in equilibrium with formaldehyde; for example, oligomers of formaldehyde and/or polymers of formaldehyde (e.g., paraformaldehyde) and/or hydrates thereof (e.g., $H_2C(OH)_2$). Amounts of a formaldehyde described herein are to be understood as encompassing molar equivalents of formaldehyde in embodiments utilizing, e.g., oligomers and/or polymers of formaldehyde.

In exemplary embodiments, 1,3,5-trioxane (a formaldehyde trimer, which is also referred to herein simply as "trioxane") is a formaldehyde contacted with 1-pentene (optionally anhydrous trioxane). 1 mole of trioxane is considered herein as equivalent to 3 moles of formaldehyde.

In some of any of the embodiments described herein, 1-pentene is contacted with 1,3,5-trioxane in the presence of $AlCl_3$ (e.g., under conditions and/or in proportions according to any of the respective embodiments described herein).

Contacting of 1-pentene with a formaldehyde is optionally effected at a controlled temperature, for example, at a temperature of no more than 20° C., at a temperature of no more than 10° C. (e.g., in a range of from −5° C. to 10° C.), at a temperature of no more than 5° C. (e.g., in a range of from −5° C. to 5° C.), or at a temperature of no more than 2° C. (e.g., in a range of from −5° C. to 2° C.).

In order to maintain a reaction temperature within a controlled temperature range (e.g., according to any of the embodiments described herein), the contacting of 1-pentene and a formaldehyde may be effected gradually (e.g., gradually adding 1-pentene and/or a formaldehyde to the Lewis acid, which may optionally initiate a reaction by acting as a catalyst), for example, such that an exothermicity of the reaction does not result in excess heating of the reaction mixture. A precise rate suitable of such contacting may depend, for example, on the nature of the equipment and cooling systems, and is well within the capabilities of the skilled person.

In addition, according to some embodiments, the time of the contacting of 1-pentene and a formaldehyde should also not be too long in duration. Excessive contacting time may be associated with undesirable side reaction, such as, e.g., polymerization. In some of any of the respective embodiments described herein, the time of the contacting of 1-pentene and a formaldehyde is no more than 24 hours, or no more than 12 hours, or no more than 6 hours, or no more than 3 hours, or no more than 2 hours, or no more than 1 hour, or no more than 30 minutes.

In exemplary embodiments, contacting 1-pentene with a formaldehyde (according to any of the respective embodiments described herein) comprises adding a mixture containing 1-pentene and a formaldehyde to the Lewis acid (which may optionally initiate a reaction by acting as a catalyst) over the course of no more than two hours (e.g., from 1.5 to 2 hours).

A polar solvent may optionally be used as a solvent for the 1-pentene, formaldehyde and/or Lewis acid according to any of the embodiments described herein. Preferably, the polar solvent is an aprotic polar solvent, for example, acetonitrile, pyridine, an ester (e.g., ethyl acetate, propylene carbonate), an ether (e.g., tetrahydrofuran), a ketone (e.g., acetone), an amide (e.g., dimethyl formamide, N-methyl-2-pyrrolidone), dimethyl sulfoxide, and/or a halogenated hydrocarbon. In some embodiments, the solvent is a halogenated hydrocarbon such as, for example, chloroform, bromoform, dichloromethane, and similar solvents. Dichloromethane is an exemplary solvent.

It is to be understood that the terms "crude" and "crude mixture", as used herein, are merely intended to identify a mixture obtained at an intermediate stage of the process (e.g., after contacting 1-pentene and a formaldehyde), and are not intended to be limiting with respect to the composition of the mixture.

The 3-hexenol in the crude first mixture (according to any of the respective embodiments described herein) optionally comprises a combination of trans-3-hexen-1-ol and cis-3-hexen-1-ol. In some such embodiments, a ratio of trans-3-hexen-1-ol to cis-3-hexen-1-ol in the crude first mixture is in a range of from 6:4 to 9:1 (trans:cis). In some embodiments, the ratio of trans-3-hexen-1-ol to cis-3-hexen-1-ol in the crude mixture is in a range of from 7:3 to 8:2 (trans:cis). In some embodiments, the trans:cis ratio in the crude mixture is substantially the same (i.e., differs by no more than 50%, optionally by no more than 20%, and optionally by no more than 10%) as the trans:cis ratio in the composition obtained at the end of the process.

According to some embodiments, the process further comprises processing the crude first mixture so as to obtain a first mixture enriched in 3-hexen-1-ol (relative to the crude mixture), which is also referred to herein as enriched first mixture, and which may optionally further comprises a chlorinated pyran (e.g., chlorinated tetrahydropyran) present in the crude mixture (e.g., according to any of the respective embodiments described herein). In some embodiments, the obtained first mixture is enriched in 3-hexen-1-ol as well as in the chlorinated pyran (relative to the crude mixture). Distillation of the crude mixture is an exemplary technique for obtaining a mixture enriched in 3-hexenol (enriched first mixture).

As exemplified herein, processing the crude first mixture (e.g., distilling the crude mixture) so as to increase the concentration of 3-hexenol therein (and optionally the concentration of chlorinated pyran therein) can reduce the amount of isomers (such as 4-hexen-1-ol and 2-hexen ol) formed upon contacting with the base at the following step.

Herein, the term "enriched" refers to any increase in concentration (e.g., of 3-hexenol) relative to an initial concentration (e.g., of a crude first mixture as described herein).

In some of any of the respective embodiments, a concentration of 3-hexenol in the mixture enriched in 3-hexenol (enriched first mixture) is at least 1.5-fold (i.e., 50% greater than) the concentration of 3-hexenol in the crude mixture. In some embodiments, the concentration of 3-hexenol in the mixture enriched in 3-hexenol is at least 2-fold (i.e., twice) the concentration of 3-hexenol in the crude mixture.

In some of any of the respective embodiments, a concentration of 3-hexenol in the mixture enriched in 3-hexenol is at least 50% by weight (and optionally at least 1.5-fold or at least 2-fold the concentration of 3-hexenol in the crude mixture). In some embodiments, the concentration of 3-hexenol in the mixture enriched in 3-hexenol is at 60% by weight (and optionally at least 1.5-fold or at least 2-fold the concentration of 3-hexenol in the crude mixture). In some embodiments, the concentration of 3-hexenol in the mixture enriched in 3-hexenol is at 70% by weight (and optionally at least 1.5-fold or at least 2-fold the concentration of 3-hexenol in the crude mixture). In some embodiments, the concentration of 3-hexenol in the mixture enriched in 3-hexenol is at 80% by weight (and optionally at least 1.5-fold or at least 2-fold the concentration of 3-hexenol in the crude mixture). In some embodiments, the concentration of 3-hexenol in the mixture enriched in 3-hexenol is at 90% by weight (and optionally at least 1.5-fold or at least 2-fold the concentration of 3-hexenol in the crude mixture).

Processing of the crude first mixture is preferably performed using any suitable equipment known in the art, such as acid-resistant equipment (e.g., formed from glass and/or with glass lining).

In some of any of the embodiments described herein, the process comprises:

(a) contacting 1-pentene with a formaldehyde in the presence of a Lewis acid to thereby obtain a crude (first) mixture comprising 3-hexen-1-ol (according to any of the respective embodiments described herein);

(b) distilling the crude mixture to thereby obtain a (first) mixture enriched in 3-hexen-1-ol (according to any of the respective embodiments described herein), the enriched mixture optionally further comprising (and optionally being enriched in) at least one chlorinated tetrahydropyran (e.g., 3-ethyl-4-chloro-tetrahydropyran); and (c) contacting the (first) mixture enriched in 3-hexen-1-ol with a base, optionally reducing an amount of chlorinated tetrahydropyran (e.g., 3-ethyl-4-chloro-tetrahydropyran) by elimination of chlorine atoms (according to any of the respective embodiments described herein).

In some of any of the embodiments described herein, the base comprises a hydroxide salt (e.g., a metal hydroxide and/or a quaternary ammonium hydroxide), an amide salt (e.g., $NaNH_2$, $LiN(C_2H_5)_2$ and/or $LiN(CH(CH_3)_2)_2$), a hydride salt (e.g., NaH) and/or a guanidine (e.g., $HNC(NH_2)_2$ or substituted derivative thereof). In some such embodiments, the base is a metal hydroxide, optionally an alkali metal hydroxide, e.g., sodium hydroxide, potassium hydroxide or lithium hydroxide. Potassium hydroxide is an exemplary base.

In some of any of the respective embodiments described herein, following the contact with a base (according to any of the respective embodiments described herein), the total concentration of chlorinated pyrans remaining in the mixture is no more than 0.5% by weight, optionally no more than 0.2% by weight, optionally no more than 0.1% by weight, optionally no more than 0.05% by weight, optionally no more than 0.02% by weight, optionally no more than 0.01% by weight, and optionally no more than 0.005% by weight.

In some of any of the embodiments described herein, following the contact with a base (according to any of the respective embodiments described herein), the total concentration of chlorinated tetrahydropyrans remaining in the mixture is no more than 0.5% by weight, optionally no more than 0.2% by weight, optionally no more than 0.1% by weight, optionally no more than 0.05% by weight, optionally no more than 0.02% by weight, optionally no more than 0.01% by weight, and optionally no more than 0.005% by weight.

In some of any of the embodiments described herein, following the contact with a base (according to any of the respective embodiments described herein), the concentration of 3-ethyl-4-chloro-tetrahydropyran remaining in the mixture is no more than 0.2% by weight, optionally no more than 0.1% by weight, optionally no more than 0.05% by weight, optionally no more than 0.02% by weight, optionally no more than 0.01% by weight, and optionally no more than 0.005% by weight.

Contacting a mixture comprising 3-hexenol (a crude first mixture or an enriched first mixture) with a base according to any of the respective embodiments described herein) is optionally effected at a temperature of at least 50° C. (e.g., from 50 to 150° C.), or at least 75° C. (e.g., from 75 to 125° C.), or at least 100° C.

In some of any of the embodiments described herein, the 3-hexenol mixture (a crude first mixture or an enriched first mixture) is added gradually to a composition comprising the base (e.g., further comprising a solvent such as polyethylene glycol), or vice versa. Such gradual addition is optionally effected gradually over the course of (during a time period of) at least 30 minutes, for example, from 30 minutes to 6 hours, or from 1 hour to 3 hours or from 1 hour to 2 hours, or about 90 minutes.

Contacting a mixture comprising 3-hexenol (a crude first mixture or an enriched first mixture) with a base according to any of the respective embodiments described herein is optionally effected for a duration (e.g., a duration after all of the 3-hexenol mixture and base have been combined) over the course of at least 2 hours (e.g., from 2 to 24 hours), or at least 4 hours (e.g., from 4 to 12 hours, or from 5 to 7 hours).

Contacting a mixture comprising 3-hexenol (a crude first mixture or an enriched first mixture) with a base according to any of the respective embodiments described herein results in a mixture which is also referred to herein as a second mixture (e.g., a second crude mixture).

In some of any of the embodiments described herein, the process further comprises separating the 3-hexenol from other compounds in the (crude second) mixture (e.g., at least one product of elimination of chlorine atoms) following the contact with a base (e.g., according to any of the embodiments described herein). In some such embodiments, a composition according to any of the respective embodiments described herein is obtained upon such separation.

As exemplified herein, separating the 3-hexenol from products of elimination of chlorine atoms may readily and conveniently be effected by distillation of the mixture containing 3-hexenol and elimination product(s) (a crude second mixture, a mixture obtained upon contact with a base, according to any of the embodiments described herein).

The distillation may be performed as described in the Examples section that follows.

Applications:

As described herein, compositions according to any of the respective embodiments described herein comprise cis-3-hexen-1-ol and/or trans-3-hexen-1-ol. Such odoriferous compounds, obtainable by a process as described herein, can be advantageously incorporated an odor-imparting (fragrance) formulations and/or in articles-of-manufacturing where including such an odor-imparting agent is beneficial.

According to an aspect of some embodiments of the present invention there is provided an odor-imparting formulation (a fragrance formulation) comprising the composition as described herein in any of the respective embodiments. In some embodiments, the odor-imparting formulation comprises at least one additional odoriferous substance (i.e., other than the composition). Alternatively or additionally, the odor-imparting formulation may optionally comprise at least one additional component which is not an odoriferous substance, such as an acceptable carrier (e.g., alcoholic or water-containing carrier). The acceptable carrier may optionally be cosmetically acceptable, agriculturally acceptable, edible, and/or suitable for a detergent.

The phrase "odoriferous substance", as used herein and in the art, describes a chemical substance or a mixture of chemical substances featuring an odor which is commonly conceived as pleasant.

The 3-hexenol can be employed in widely varying amounts, depending upon the specific application and on the nature and quantity of other odorant ingredients, if present and/or the relative proportions of trans-3-hexen-1-ol and cis-3-hexen-1-ol. The proportion of 3-hexenol is typically from 0.001 to 20 weight percents of the total weight of the article-of-manufacturing or formulation containing same, but can also be up to 50 weight percents. The composition containing 3-hexenol, as described herein, can be employed in widely varying amounts (e.g., in an odor-imparting formulation and/or article-of-manufacturing, as described herein), depending upon the specific concentration of 3-hexenol in the composition, a ratio trans-3-hexen-1-ol and cis-3-hexen-1-ol, and/or the nature and quantity of other odorant ingredients, if present.

The odor-imparting formulation according to any of the embodiments described herein may be provided as a fragrance concentrate and/or as a fragrance formulation which can be incorporated an article-of-manufacturing as described herein.

According to an aspect of some embodiments of the present invention, there is provided an article-of-manufacturing comprising a composition and/or odor-imparting-formulation as described herein.

In some embodiments, the articles-of-manufacturing include products to which the addition of an odor-imparting agent is beneficial.

In some embodiments, the articles of manufacturing include body care products, including bath/shower gels, hair conditioners, shampoos, liquid soaps, tablet soaps, cosmetic products and talcum powders; perfume products, particularly alcoholic perfumes; cleansing products or compositions such as liquid detergents; fabric care products such as fabric softeners; and in lifestyle products, such as pot pourri and incense.

Non-limiting examples of such article-of-manufacturing include, baby care, beauty care, fabric and home care, family care, feminine care, health care, snack and/or beverage products, and, more specifically, but without limitation, fine fragrance products or formulations (e.g. perfumes, colognes, eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling formulations or products; deodorants and antiperspirants, personal cleansing, cosmetics and skin care products or formulations, including creams, lotions, and other topically applied products, and shaving products; products for and/or methods relating to treating fabrics, hard surfaces and any other surfaces in the area of fabric and home care, including air care, car care, dishwashing, fabric conditioning (including softening), laundry detergent, laundry and rinse additive and/or care, hard surface cleaning and/or treatment, and other cleaning compositions; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening.

As used herein, the term "cleansing composition" includes washing agents, especially cleaning detergents, liquid, gel or paste-form all-purpose washing agents, liquid fine-fabric detergents, hand dishwashing agents or light duty dishwashing agents, machine dishwashing agents, including the various tablet, granular, liquid and rinse-aid types, cleaning and disinfecting agents, including antibacterial hand-wash types, cleaning bars, mouthwashes, denture cleaners, dentifrice, car or carpet shampoos, bathroom cleaners, hair shampoos and hair-rinses, shower gels and foam baths and metal cleaners, as well as cleaning auxiliaries such as bleach additives and "stain-stick" or pre-treat types, substrate-laden products such as dryer added sheets, dry and wetted wipes and pads, nonwoven substrates, and sponges, as well as sprays and mists.

As used herein, the term "fabric care composition" includes, unless otherwise indicated, fabric softening compositions, fabric enhancing compositions, fabric freshening compositions and combinations thereof.

The 3-hexenol-containing composition and/or odor-imparting formulation of the present embodiments can be used in combination with one or more other odor-imparting agents (fragrances).

The composition of the present embodiments may be employed simply by directly mixing it, or a fragrance formulation containing same, with the article-of-manufacturing to which it is applied. Optionally, the composition or a fragrance formulation containing same may be entrapped or embedded in a delivery system such as, for example, polymers, capsules, microcapsules and nanocapsules, liposomes, film formers, absorbents such as carbon or zeolites, cyclic oligosaccharides, and mixtures thereof, or may be chemically bonded to substrates, which are adapted to release the odoriferous substance(s) upon application of an external stimulus such as light, enzyme, or the like, and then applied to the article-of-manufacturing.

Embodiments of the present invention thus further encompass methods of manufacturing articles-of-manufacturing as described herein, which comprise incorporating an odoriferous substance or an odor-imparting formulation containing same in the article-of-manufacturing, typically using conventional techniques and methods. Through the addition of the odoriferous substance of the present embodiments, the odor notes of the article-of-manufacturing may be improved, enhanced or modified.

It is expected that during the life of a patent maturing from this application many relevant article-of-manufacturing to which an odoriferous substance is beneficially added will be developed and the scope of the term "article-of-manufacturing" is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical arts.

Herein, the term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms (C(1-4) alkyl) or even 1 to 3 carbon atoms (C(1-3) alkyl). Exemplary alkyls include methyl, ethyl and propyl, preferably unsubstituted.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Exemplary Processes of Preparing 3-Hexenol

According to some of the present embodiments, 1-pentene is reacted with 1,3,5-trioxane (as a source of formaldehyde) to obtain a crude mixture containing 3-hexenol (a crude first mixture), followed by reaction of chlorinated byproducts with a base (e.g., potassium hydroxide), according to the exemplary synthetic scheme depicted in FIG. 2.

In one exemplary process, 1-pentene was reacted with 1,3,5-trioxane to obtain crude 3-hexenol on a large scale, as follows.

Mixture 1 was prepared from 250 kg trioxane (corresponding to 8.3 kmol formaldehyde), 582 kg 1-pentene (882 liters, 8.3 kmol) and 665 kg dichloromethane (DCM), which were charged into a feeding reactor and mixed, Mixture 2 was prepared by charging 8116 kg DCM into the reactor followed by 665 kg of $AlCl_3$ (4.98 kmol) at 0° C.

After preparing Mixture 2 in the reactor, it was cooled to −5° C. Mixture 1 was added drop-wise over the course of 1.5-2 hours, maintaining the temperature in a range of −5° C. to 2° C.

Figure 3:
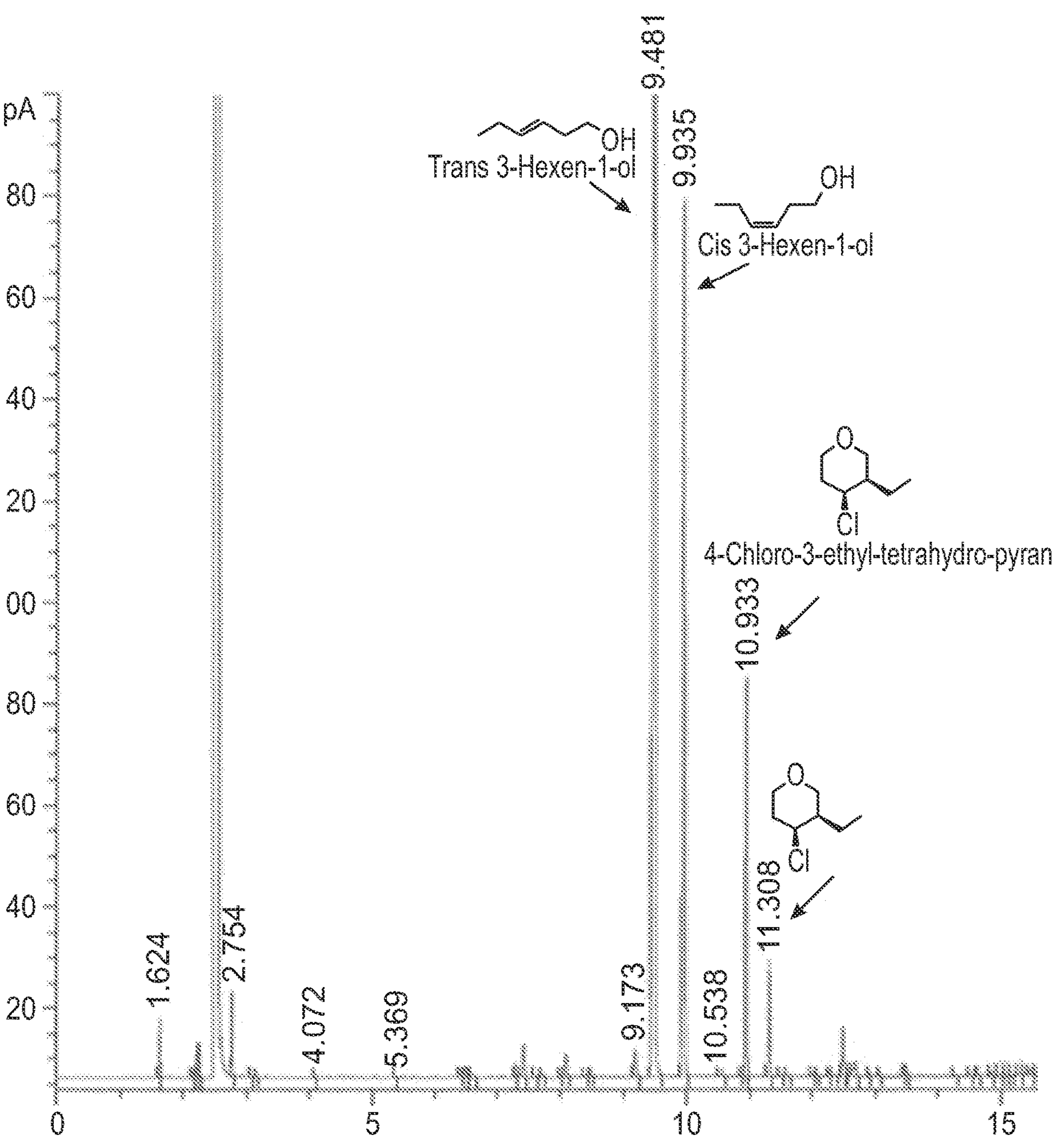
FIG. 3 presents a gas chromatography spectrum of a crude mixture (a crude first mixture) obtained in an initial step of a large scale preparation of 3-hexen-1-ol according to some embodiments of the invention (x-axis indicates retention time in minutes; retention time). The peak at 9.173 is for 1-hexanol. The peaks around 10.5 are for 4-hexen-1-ol and 2-hexen-1-ol.

Once the addition was completed, mixing was performed for 15 minutes and the reaction mixture was added to a cooled 3588 kg 2% HCl up until 15° C. After addition was completed, the obtained mixture was stirred at 10° C. for 15 minutes, followed by waiting for phase separation for 15 minutes. The organic phase was then washed with 3046 kg 10% $NaHCO_3$ (pH=8.5-9) at 10° C., then mixed for 15 minutes, followed by waiting for phase separation for 15 minutes. DCM was then recovered at a temperature of 45° C. and pressure of 650-330 mbar with a short column, and 1008 kg of crude (crude first mixture) was obtained, containing 38% 3-hexenol with 4-6% chloropyran derivative (primarily 3-ethyl-4-chloro-tetrahydropyran), as determined by gas chromatography. A gas chromatography spectrum of the obtained crude showed predominant peaks associated with trans-3-hexen-1-ol (at 9.481 minutes) and cis-3-hexen-1-ol (at 9.935 minutes), as is shown in FIG. 3, with smaller but substantial peaks (at 10.933 and 11.308 minutes) associated with stereoisomers of 3-ethyl-4-chloro-tetrahydropyran.

Gas chromatography analysis was performed using a 7693 instrument (Agilent Technologies), with an injection volume of 1 μl, inlet split ratio of 90:1 and temperature of 250° C., ZB-WAX column (Restek) (polyethylene glycol capillary column phase, 30 m length, 0.25 mm internal diameter, 0.25 μm film thickness, 16.371 psi head pressure), and flame ionization detector (FID) (T=260° C., air flow of 360 ml/minute, $H_2$ flow of 30 ml/minute and He makeup of 24.8 ml/minute). Samples were diluted to 2% in dichloromethane. The temperature was raised from 50° C. to 100° C. at a rate of 5° C. per minute, then from 100° C. to 220° C. at a rate of 10° C. per minute, followed by 3 minutes at 220° C. (total of 25 minutes).

The procedures described hereinabove were performed several times, until a total of 3378 kg of crude (crude first mixture) was obtained, which was then distilled to obtain 1362 kg of an enriched mixture containing 85% 3-hexenol with 6-8% chloropyran derivatives (primarily 3-ethyl-4-chloro-tetrahydropyran) (enriched first mixture). Distillation was performed using glass filled column with 2-30 or 2-20 or 2-10, or 2-8 theoretical plates.

The enriched first mixture was then treated with KOH (potassium hydroxide) to dechlorinate the chloropyran derivative, so as to obtain a second mixture as described herein.

When dechlorination was performed without the previous step of distillation to obtain an enriched mixture, a significant increase was observed in 3-hexenol isomers, such as 2-hexenol and 4-hexenol. These isomers are difficult to separate from 3-hexenol by subsequent distillation, and have an undesirable effect on the odor of the product.

Figure 4:
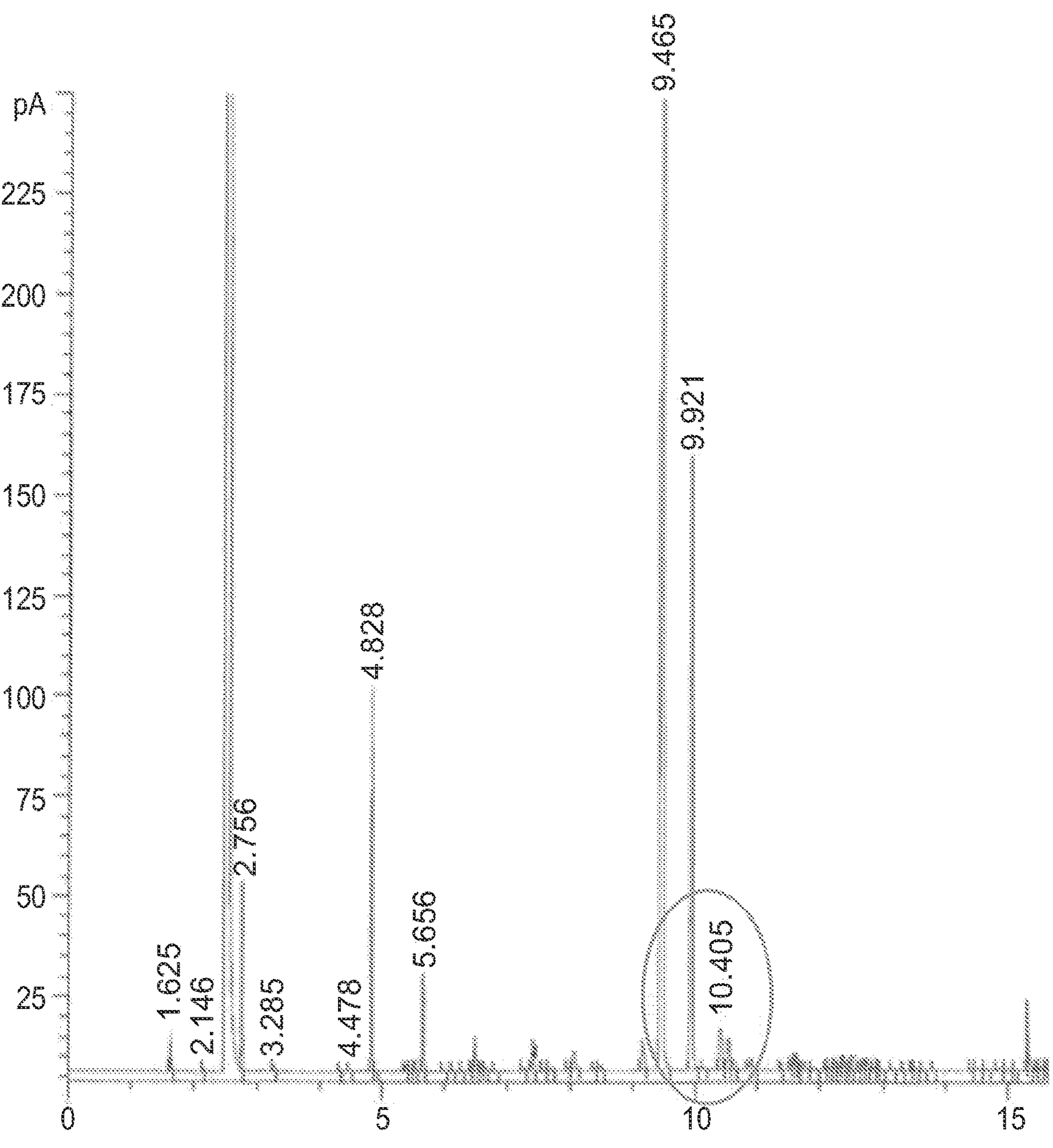
FIG. 4 presents a gas chromatography spectrum of a sample (crude second mixture) following elimination of chlorine (as HCl) from a chlorinated pyran derivative byproduct in a crude (second) mixture of 3-hexen-1-ol according to some embodiments of the invention (x-axis indicates retention time in minutes). The peaks around 4.8 minutes are for the elimination products of chlorinated pyran derivative (which are easily removed by a following distillation). The circle around 10 minutes shows reduced amount of chlorinated pyran derivatives and of 2-hexen-1-ol and 4-hexen-1-ol.

442 kg PEG400 (1.1 kmol) were charged into the reactor followed by 247 kg KOH (3.9 kmol), and the obtained mixture was heated to 100° C. 1362 kg of the enriched 3-hexenol distillate described hereinabove (85% 3-hexenol and 6-8% chloropyran derivative; enriched first mixture) was then added drop-wise over the course of 1.5 hours, while maintaining the temperature at 100° C. The reaction mixture was then stirred for 5-7 hours until the concentration of chloropyran derivative was no more than 0.05%, as determined by gas chromatography. Upon completion of the reaction, the mixture was cooled to room temperature and 741 kg water was added, followed by heating the mixture to 60° C. for 0.5 hour and phase separation. 680 kg of saturated $NH_4Cl$ was then added to the organic phase at room temperature, and the phases were mixed and then separated. 1227 kg of crude (crude second mixture) was obtained with 85% 3-hexenol (80:20 ratio of trans:cis) and no more than 0.1% chloropyran derivative, as determined by gas chromatography. A gas chromatography spectrum of the obtained crude (without chloropyran derivative) showed the predominant peaks associated with trans-3-hexen-1-ol (at 9.465 minutes) and cis-3-hexen-1-ol (at 9.921 minutes) without noticeable peaks associated with 3-ethyl-4-chloro-tetrahydropyran, as is shown in FIG. 4.

The crude product (crud second mixture) was then subjected to a final distillation, which afforded 1,000 Kg of 3-hexenol (80:20 ratio of trans:cis), having a purity of about 97%, as determined by gas chromatography, and containing less than 0.1% chloropyran derivative(s), and about 1-3% 1-hexanol. The final distillation was performed using a column with 10-60 or 20-50 or 20-40 theoretical plates.

Example 2

Effect of Chloropyran Derivative on Scent of 3-Hexenol

A crude composition of 3-hexenol without chloropyran derivative, prepared according to procedures as described in Example 1 was prepared, and then distilled to obtain 3-hexenol (at a trans:cis ratio of 72.5:27.5) at a concentration of at least 97% by weight. The scent of this composition was compared with that of similar 3-hexenol compositions which had 0.1% or 0.3% by weight of 3-ethyl-4-chloro-tetrahydropyran.

The 3-hexenol (>97%) without chloropyran derivative exhibited a powerful and intensely green, grassy odor.

The 3-ethyl-4-chloro-tetrahydropyran alone exhibited a harsh, solvent-like odor. At a concentration of 0.3% by weight (in 3-hexenol), the harshness of the 3-ethyl-4-chloro-tetrahydropyran was noticeable in the scent of the mixture. At a concentration of 0.1% by weight (in 3-hexenol), the odor of the 3-ethyl-4-chloro-tetrahydropyran was masked by that of 3-hexenol.

These results indicate significant advantages of reduced levels of chloropyran derivatives in 3-hexenol compositions.

The green, grassy odor of 3-hexenol (>97%) was maintained unmasked in the presence of 1-hexanol at a concentration of 1-3%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A process of preparing a composition comprising 3-hexen-1-ol, the process comprising:

(a) contacting 1-pentene with a formaldehyde in the presence of a Lewis acid comprising at least one chlorine atom to obtain a crude mixture comprising 3-hexen-1-ol;

(b) distilling the crude mixture to obtain a mixture of 3-hexen-1-ol and undesired chlorinated tetrahydropyran by-product;

(c) contacting said mixture of 3-hexen-1-ol and undesired chlorinated tetrahydropyran by-product with a base selected from sodium hydroxide and potassium hydroxide at a temperature of between 50° C. to 150° C. to reduce an amount of the chlorinated tetrahydropyran by elimination of a chlorine atom; and (d) separating 3-hexen-1-ol by distillation.

2. The process of claim 1, wherein a concentration of 3-hexen-1-ol in said composition is at least 95% by weight, based on the weight of the total composition.

3. The process of claim 2, wherein said composition comprises trans-3-hexen-1-ol at a concentration in a range of from 67% to 82% by weight, based on the weight of the total composition, and cis-3-hexen-1-ol at a concentration in a range of from 18% to 33% by weight, based on the weight of the total composition.

4. The process of claim 3, wherein a ratio of trans-3-hexen-1-ol to cis-3-hexen-1-ol in said composition is in a range of from 7:3 to 8:2 (trans:cis).

5. The process of claim 2, wherein a total concentration of 2-hexen-1-ol and 4-hexen-1-ol in the composition is no more than 0.25% by weight, based on the weight of the total composition.

6. The process of claim 1, wherein a total concentration of chlorinated tetrahydropyran in the composition after contacting with the base is no more than 0.1% by weight, based on the weight of the total composition.

7. The process of claim 1, wherein the tetrahydropyran comprises 3-ethyl-4-chloro-tetrahydropyran.

8. The process of claim 1, wherein the formaldehyde is 1,3,5-trioxane.

9. The process of claim 1, wherein the Lewis acid is $AlCl_3$.

10. The process of claim 1, wherein the composition comprises:

(a) trans-3-hexen-1-ol in a concentration range of 67% to 82% by weight, based on the weight of the total mixture, and cis-3-hexen-1-ol in a concentration range of 18% to 33% by weight, based on the weight of the total composition;

(b) trans-3-hexen-1-ol and cis-3-hexen-1-ol in a concentration of at least 95% by weight, based on the weight of the total composition;

(c) 2-hexen-1-ol and 4-hexen-1-ol in a concentration of 0.25% or less by weight, based on the weight of the total composition; and (d) 3-ethyl-4-chloro-tetrahydropyran in a concentration of 0.1% or less, based on the weight of the total composition.

* * * * *